US00PP08641P

United States Patent [19]

van der Knaap

[11] Patent Number: Plant 8,641

[45] Date of Patent: Mar. 15, 1994

[54] CHRYSANTHEMUM PLANT—GLASNOST CULTIVAR

[75] Inventor: Jacques C. M. van der Knaap, De Lier, Netherlands

[73] Assignee: Fides Beheer B.V., De Lier, Netherlands

[21] Appl. No.: 34,824

[22] Filed: Mar. 16, 1993

[51] Int. Cl.[5] ..... A01H 5/00

[52] U.S. Cl. ..... Plt./74.1

[58] Field of Search ..... Plt. 74.1, 82.4, 82.5, Plt. 76, 82, 81

[56] Reference Cited

U.S. PATENT DOCUMENTS

PP 4629 1/1981 Jessel, Jr. et al. ..... Plt./82.4

PP 6851 6/1989 van Wingerden ..... Plt./82.4

PP 8241 5/1993 van der Knaap ..... Plt./82.4

*Primary Examiner*—Howard J. Locker

*Attorney, Agent, or Firm*—Burns, Doane, Swecker & Mathis

[57] ABSTRACT

A new and distinct cultivar of Chrysanthemum plant named Glasnost is provided. The new cultivar was the result of a controlled breeding program. The new cultivar forms attractive single purple anemone flowers with a more intense red-purple cushion. The plant exhibits substantial resistance to leafminers, and the flowers exhibit a good vase life. The response period of the flowers is approximately eight weeks. The new cultivar is particularly suited for use in the production throughout the year of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium,* Ramat., and hereinafter is referred to by the cultivar name Glasnost.

The new cultivar is the product of a planned breeding program which had as its objective the creation of a new Chrysanthemum cultivar which exhibits attractive single purple anemone flowers having a diameter of approximately 50 mm., a flower response period of approximately eight weeks, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1988 at De Lier, The Netherlands. The female parent (i.e., the seed parent) was an unnamed plant designated 88.2683 (non-patented in the United Sates) and the male parent (i.e., the pollen parent) was the product of the pollination of the Pall Mall cultivar (non-patented in the United States) and an unnamed plant designated 85.2066 (non-patented in the United States). The parentage of the new cultivar can be summarized as follows:

88.2683×(Pall Mall×85.2066).

The seeds resulting from the above pollination were sown and plantlets were obtained which were physically and biologically different from each other. Selective study during June 1988 resulted in the identification of a single plant of the new variety.

It was found that the new cultivar of the present invention:

(a) exhibits attractive single purple anemone flowers with a more intense red-purple cushion having an overall diameter of approximately 50 mm., (b) exhibits a flower response period of approximately eight weeks, (c) forms flowers that exhibit a good vase life, (d) exhibits a substantial resistance to leafminers, and (e) has the ability to produce flowers of commercially acceptable quality throughout the year in a cut mum production program.

The new cultivar exhibits limited resistance to low temperatures.

Asexual reproduction of the new cultivar by cuttings initially taken during August 1988, as performed at De Lier, The Netherlands, in a controlled environment has demonstrated that the characteristics of the new cultivar as herein disclosed are firmly fixed and are retained through successive generations of asexual propagation.

Glasnost has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Wall Street cultivar (U.S. Plant Pat. No. 6,869), the Glasnost cultivar is found to exhibit a faster response period of approximately 8 weeks vs. 9 weeks, a smaller flower size of approximately 50 mm. vs. 60 mm.), less vigor, superior leafminer resistance, and more intensely colored ray florets. The flower type, foliage size and foliage color, are similar to that exhibited by the Wall Street cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, during the spring of 1990. The plants described were grown under standard greenhouse conditions which approximate those commonly utilized for the production of cut mums.

Classification:

*Botanical.*—*Chrysanthemum morifolium* Ramat., cv. Glasnost.

*Commercial.*—Cut anemone spray.

INFLORESCENCE

A. Capitulum:

*Form.*—Single.

*Type.*—Anemone.

*Diameter across face.*—Approximately 50 mm. on average.

*Diameter across disc.*—Approximately 25 mm. on average.

B. Corolla of ray and disc florets:

*Color (General tonality from a distance of three meters).*—Rose Purple, Purple Group 75B.

*Color disc florets.*—The cushion is a more intense red purple that approximates Red-Purple Group 74D.

C. Reproductive organs:

*Androecium.*—Present in disc florets and absent in ray florets.

*Gynoecium.*—Present in disc florets and in ray florets.

PLANT

A. General appearance:

*Height.*—Approximately 80 cm. on average.

B. Foliage:

*Color (upper surface).*—Green Group 137A.

*Color (under surface).*—Green Group 138A.

I claim:

1. A new and distinct cultivar of Chrysanthemum plant named Glasnost substantially as herein shown and described, which:

(a) exhibits attractive single purple anemone flowers with a more intense red-purple cushion having an overall diameter of approximately 50 mm., (b) exhibits a flower response period of approximately eight weeks, (c) forms flowers that exhibit a good vase life, (d) exhibits a substantial resistance to leafminers, and (e) has the ability to produce flowers of commercially acceptable quality throughout the year in a cut mum production program.

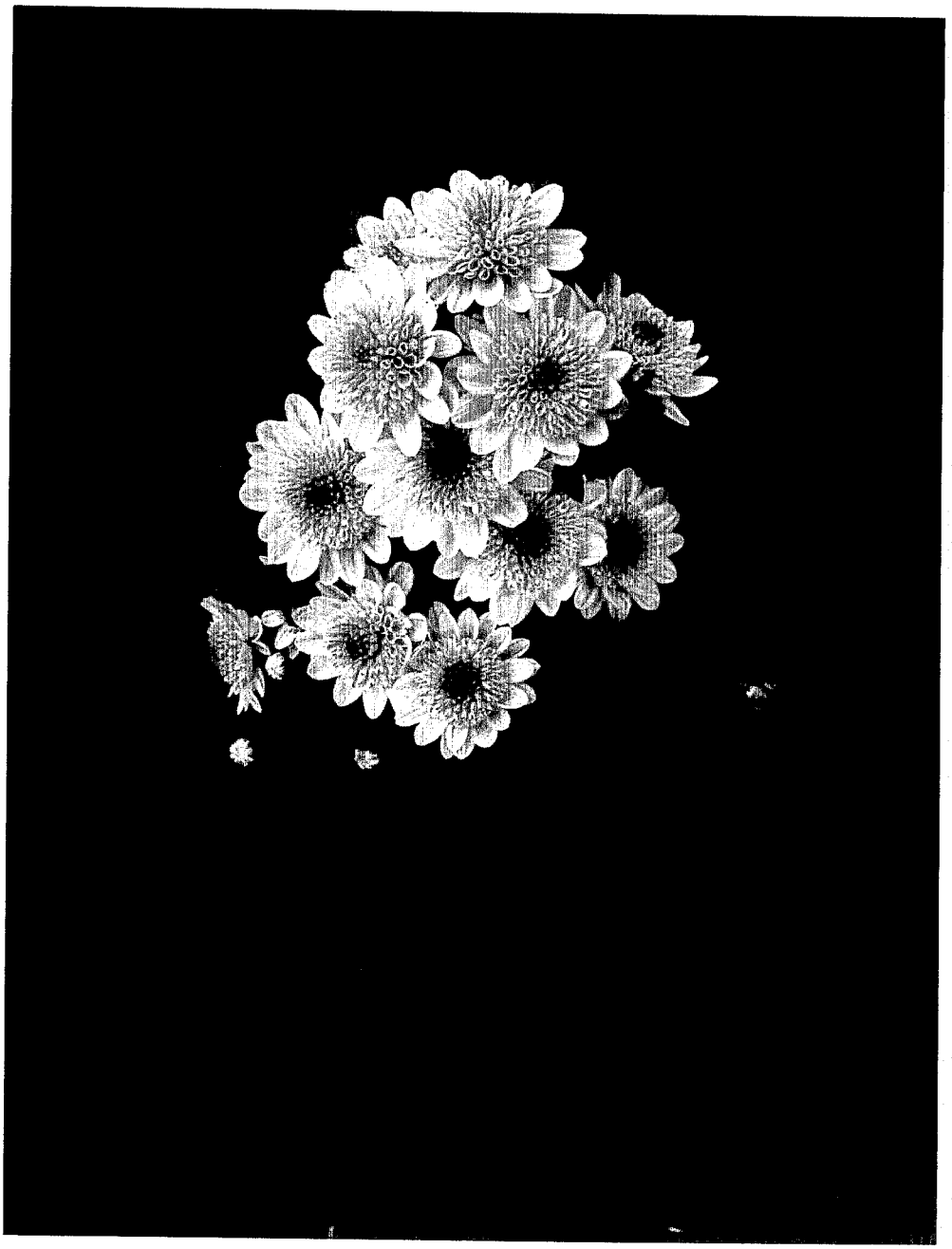

* * * * *